United States Patent
Nakano

(10) Patent No.: US 10,473,617 B2
(45) Date of Patent: Nov. 12, 2019

(54) GAS DETECTION APPARATUS

(71) Applicant: NGK Spark Plug Co., LTD., Nagoya (JP)

(72) Inventor: Yoshihiro Nakano, Komaki (JP)

(73) Assignee: NGK Spark Plug Co., LTD., Nagoya (JP)

(*) Notice: Subject to any disclaimer, the term of this patent is extended or adjusted under 35 U.S.C. 154(b) by 150 days.

(21) Appl. No.: 15/433,663

(22) Filed: Feb. 15, 2017

(65) Prior Publication Data

US 2017/0234831 A1 Aug. 17, 2017

(30) Foreign Application Priority Data

Feb. 17, 2016 (JP) ................. 2016-028246

(51) Int. Cl.
*G01N 27/416* (2006.01)
*G01N 27/406* (2006.01)
*G01N 27/409* (2006.01)

(52) U.S. Cl.
CPC ....... *G01N 27/4163* (2013.01); *G01N 27/409* (2013.01); *G01N 27/4067* (2013.01)

(58) Field of Classification Search
CPC ........... G01N 27/4163; G01N 27/4067; G01N 27/409
See application file for complete search history.

(56) References Cited

U.S. PATENT DOCUMENTS 6,336,354 B1 * 1/2002 Suzuki .............. G01N 27/4067 338/34
2015/0013431 A1 * 1/2015 Kakimoto ........... G01N 27/419 73/23.31

FOREIGN PATENT DOCUMENTS

JP 2013-221930 A 10/2013

* cited by examiner

*Primary Examiner* — J. Christopher Ball
(74) *Attorney, Agent, or Firm* — Leason Ellis LLP

(57) ABSTRACT

A multi-gas detection apparatus is configured such that electric power supplied from a power supply to a heater is controlled by pulse width modulation so as to control the temperature of a first solid electrolyte body. The multi-gas detection apparatus detects the concentration of ammonia by using a first ammonia detection section in which an electromotive force is generated between a first reference electrode and a first detection electrode in accordance with the concentration of ammonia in the exhaust gas. The multi-gas detection apparatus calculates the amount of a change (i.e., offset voltage) in the ammonia electromotive force caused by change in the output voltage of the power supply. The multi-gas detection apparatus corrects the ammonia electromotive force generated in the first ammonia detection section through use of the calculated change amount.

4 Claims, 5 Drawing Sheets

GAS DETECTION APPARATUS

This application claims the benefit of Japanese Patent Application No. 2016-028246, filed Feb. 17, 2016, which is incorporated herein in its entirety by reference.

FIELD OF THE INVENTION

The present invention relates to a gas detection apparatus for detecting the concentration of a gas present in an atmosphere of interest.

BACKGROUND OF THE INVENTION

In recent years, a urea SCR (Selective Catalytic Reduction) system is receiving attention as a technique for cleaning NOx-containing exhaust gas emitted from internal combustion engines such as gasoline engines and diesel engines (where NOx stands for nitrogen oxides). In the urea SCR system, ammonia ($NH_3$) is chemically reacted with nitrogen oxides (NOx) to reduce the nitrogen oxides to nitrogen ($N_2$), and the exhaust gas containing the nitrogen oxides is thereby cleaned.

In the urea SCR system, when the amount of ammonia supplied for the nitrogen oxides is excessively large, unreacted ammonia may be contained in the exhaust gas and emitted to the outside. To reduce the emission of ammonia described above, a multi-gas sensor capable of measuring the concentrations of a plurality of gases including ammonia contained in the exhaust gas is used for the urea SCR system.

In one known multi-gas sensor, an ammonia sensor including a reference electrode, a detection electrode, and a solid electrolyte body sandwiched between these electrodes is attached to an NOx sensor (see, for example, Japanese Patent Application Laid-Open (kokai) No. 2013-221930).

Problems to be Solved by the Invention

In the case where a heater energized and controlled by means of pulse width modulation is used for heating the ammonia sensor to an activation temperature at which the ammonia sensor can detect the concentration of a gas, the potential of the ground (ground level) changes instantaneously when the heater is switched between an energized state (ON state) and a deenergized state (OFF state). The solid electrolyte body of the ammonia sensor has an impedance (a resistance component and a capacitance component) between the reference electrode and the detection electrode. Therefore, when the ground level changes instantaneously, the electromotive force generated between the reference electrode and the detection electrode changes with a predetermined time constant delay, which may lower the detection accuracy of the ammonia sensor.

The present invention has been accomplished in view of the above problem, and its object is to provide a technique for improving the accuracy in detecting the concentration of a gas.

SUMMARY OF THE INVENTION

Means for Solving the Problems

The present invention accomplished so as to achieve the above-described object is a gas detection apparatus for detecting the concentration of a target gas in an atmosphere of interest. The gas detection apparatus comprises; a gas sensor having a solid electrolyte body, a pair of electrodes disposed on the solid electrolyte body, and a heater for heating the solid electrolyte body, a change amount calculation section and a correction section. In the gas detection apparatus, electric power supplied from a power supply to the heater is controlled by pulse width modulation so as to control the temperature of the solid electrolyte body. The gas detection apparatus detects the concentration of the target gas through use of an electromotive force generated between the pair of electrodes in accordance with the concentration of the target gas. The atmosphere of interest is a gas atmosphere to be detected by the gas detection apparatus.

The gas detection apparatus of the present invention comprises a change amount calculation section and a correction section. The change amount calculation section calculates the amount of a change in the electromotive force caused by a change in an output voltage of the power supply. The correction section corrects the electromotive force generated in the gas sensor through use of the change amount calculated by the change amount calculation section.

By virtue of the above-described configuration, the gas detection apparatus of the present invention can reduce the influence of changes in the electromotive force which occur due to changes in the output voltage of the power supply, to thereby improve the accuracy in detecting the gas concentration.

The gas detection apparatus of the present invention may comprise an oxygen detection section which detects the concentration of oxygen in the atmosphere of interest. In this case, the change amount calculation section may correct the change amount on the basis of the concentration of oxygen detected by the oxygen detection section.

By virtue of the above-described configuration, the gas detection apparatus of the present invention can reduce the influence of changes in the electromotive force which occur when the impedance of the gas sensor changes in accordance with the concentration of oxygen in the atmosphere of interest, to thereby further improve the accuracy in detecting the gas concentration.

In the gas detection apparatus of the present invention, the correction section may correct the electromotive force by subtracting the change amount calculated by the change amount calculation section from the electromotive force generated in the gas sensor.

By virtue of the above-described configuration, the gas detection apparatus of the present invention can correct the electromotive force by a simple computation of subtracting the change amount from the electromotive force generated in the gas sensor, to thereby reduce the computation processing load of the gas detection apparatus.

In the gas detection apparatus of the present invention, the correction section may correct the electromotive force through use of the electromotive force detected after elapse of a detection time set in advance from a point in time at which the heater is switched from an energized state to a deenergized state by the pulse width modulation.

The gas detection apparatus of the present invention configured as described above detects the concentration of the target gas through use of the electromotive force detected when no electric power is supplied to the heater. Therefore, the gas detection apparatus can reduce the influence of changes in the electromotive force which occur due to the flow of current to the heater, to thereby further improve the accuracy in detecting the gas concentration.

BRIEF DESCRIPTION OF THE DRAWINGS

These and other features and advantages of the present invention will become more readily appreciated when con

DETAILED DESCRIPTION OF THE INVENTION

An embodiment of the present invention will be described with reference to the drawings.

A multi-gas detection apparatus 1 in the embodiment to which the present invention is applied is used for a urea SCR (Selective Catalytic Reduction) system that is mounted on a vehicle to thereby clean nitrogen oxide (NOx)-containing exhaust gas emitted from a diesel engine. More specifically, the multi-gas detection apparatus 1 measures, after the NOx contained in the exhaust gas is reacted with ammonia (urea), the concentrations of nitrogen monoxide (NO), nitrogen dioxide ($NO_2$), and ammonia contained in the resulting exhaust gas. The vehicle on which the multi-gas detection apparatus 1 is mounted is referred to as the "present vehicle."

Figure 1:
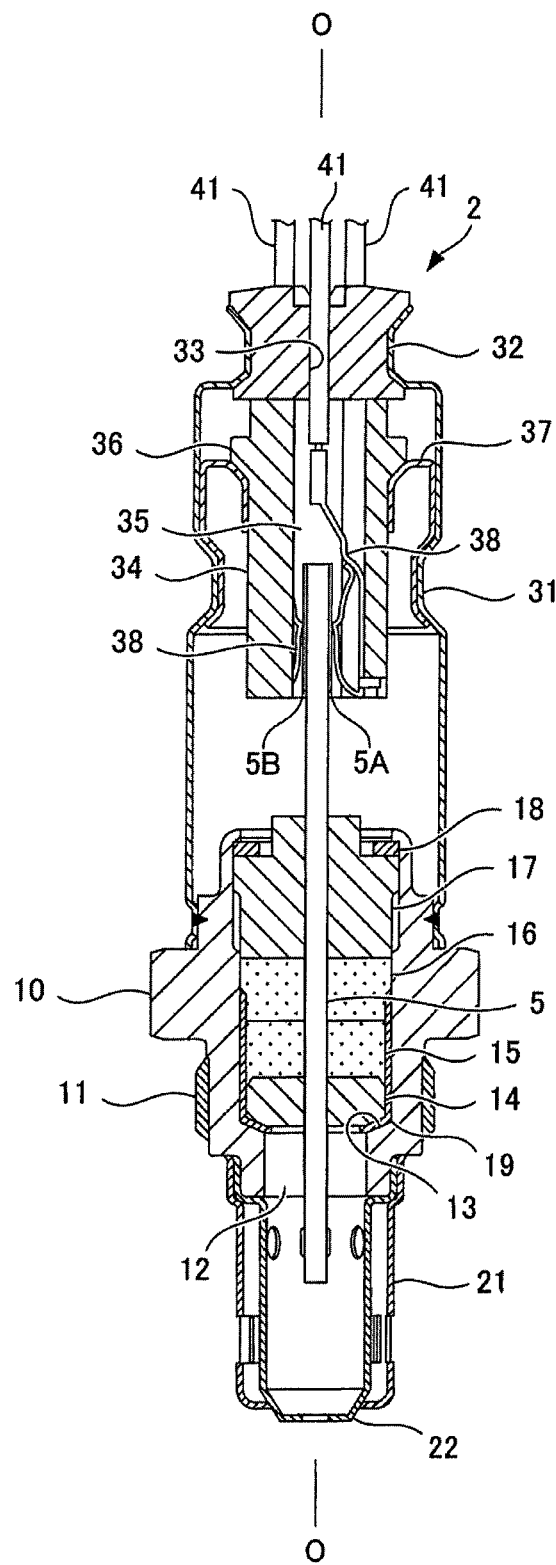
- FIG. 1 is a cross-sectional view showing the internal structure of a multi-gas sensor 2.
Figure 2:
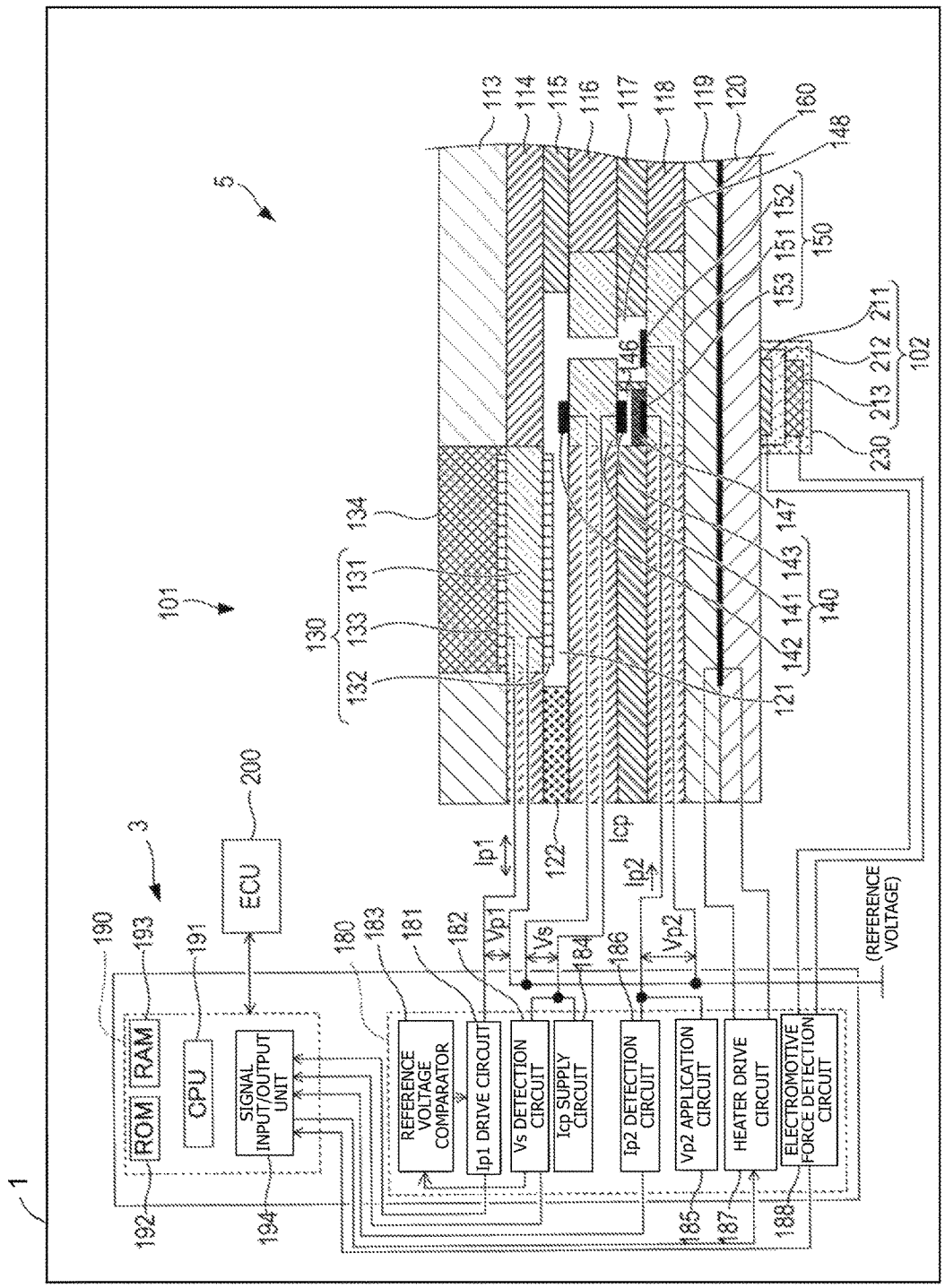
FIG. 2 is an illustration showing the schematic configuration of a sensor element unit 5 and a control section 3.

The multi-gas detection apparatus 1 includes a multi-gas sensor 2 shown in FIG. 1 and a control section 3 shown in FIG. 2.

As shown in FIG. 1, the multi-gas sensor 2 includes a sensor element unit 5, a metallic shell 10, a separator 34, and connection terminals 38. In the following description, the side of the multi-gas sensor 2 on which the sensor element unit 5 is disposed (the lower side in FIG. 1) is referred to as a forward end side, and the side on which the connection terminals 38 are disposed (the upper side in FIG. 1) is referred to as a rear end side.

The sensor element unit 5 has a plate shape extending in the direction of an axial line O. Electrode terminal portions 5A and 5B are disposed at the rear end of the sensor element unit 5. In FIG. 1, only the electrode terminal portions 5A and 5B are shown as electrode terminal portions formed in the sensor element unit 5 for the purpose of simplifying the drawing. However, in practice, a plurality of electrode terminal portions are formed according to the number of, for example, electrodes included in an NOx detection section 101, a first ammonia detection section 102 and a second ammonia detection section 103 described later.

The metallic shell 10 is a tubular member, and a threaded portion 11 used to fix the multi-gas sensor 2 to an exhaust pipe of a diesel engine is formed on the external surface of the metallic shell 10. The metallic shell 10 has a through hole 12 extending in the direction of the axial line O and a ledge 13 protruding inward in the radial direction of the through hole 12. The ledge 13 is formed as an inward tapered surface extending from the radially outer side of the through hole 12 toward its center and inclined toward the forward end side.

The metallic shell 10 holds the sensor element unit 5 with its forward end protruding from the forward end of the through hole 12 and the rear end protruding from the rear end of the through hole 12.

A ceramic holder 14 that is a tubular member surrounding the radial circumference of the sensor element unit 5, talc rings 15 and 16 that are powder filler layers, and a ceramic sleeve 17 are stacked in this order inside the through hole 12 of the metallic shell 10 from the forward end side toward the rear end side.

A crimp packing 18 is disposed between a rear end portion of the ceramic sleeve 17 and a rear end portion of the metallic shell 10. A metallic holder 19 is disposed between the ceramic holder 14 and the ledge 13 of the metallic shell 10. The metallic holder 19 holds the talc ring 15 and the ceramic holder 14. A rear end portion of the metallic shell 10 is crimped so as to press the ceramic sleeve 17 toward the forward end side through the crimp packing 18.

An outer protector 21 and an inner protector 22 are disposed at a forward end portion of the metallic shell 10. The outer protector 21 and the inner protector 22 are tubular members formed from a metallic material such as stainless steel having a closed forward end. The inner protector 22 covers a forward end portion of the sensor element unit 5 and is welded to the metallic shell 10, and the outer protector 21 covers the inner protector 22 and is welded to the metallic shell 10.

A forward end portion of an outer tube 31 formed into a tubular shape is fixed to a rear end portion of the metallic shell 10. A grommet 32 is disposed in a rear end opening of the outer tube 31 so as to close the opening.

Lead wire insertion holes 33 into which lead wires 41 are inserted are formed in the grommet 32. The lead wires 41 are electrically connected to the electrode terminal portions 5A and 5B of the sensor element unit 5.

The separator 34 is a tubular member disposed rearward of the sensor element unit 5. A space formed inside the separator 34 is an insertion hole 35 passing through the separator 34 in the direction of the axial line O. A flange portion 36 protruding radially outward is formed on the outer surface of the separator 34.

A rear end portion of the sensor element unit 5 is inserted into the insertion hole 35 of the separator 34, and the electrode terminal portions 5A and 5B are disposed inside the separator 34.

A tubular holding member 37 is disposed between the separator 34 and the outer tube 31. The holding member 37 is in contact with the flange portion 36 of the separator 34 and also with the inner surface of the outer tube 31 and thereby holds the separator 34 such that the separator 34 is fixed to the outer tube 31.

The connection terminals 38 are members disposed inside the insertion hole 35 of the separator 34 and are electrically conductive members that electrically connect the electrode terminal portions 5A and 5B of the sensor element unit 5 to their respective lead wires 41. In FIG. 1, only two connection terminals 38 are shown for the purpose of simplifying the drawing.

As shown in FIG. 2, the control section 3 of the multi-gas detection apparatus 1 is electrically connected to an electronic control unit 200 mounted on the present vehicle. The electronic control unit 200 receives data representing the concentrations of NO, $NO_2$, and ammonia in exhaust gas that are computed by the control section 3. Then the electronic control unit 200 performs processing for controlling the operating conditions of the diesel engine according to the data received and also performs cleaning processing for NOx accumulated on a catalyst.

Figure 3:
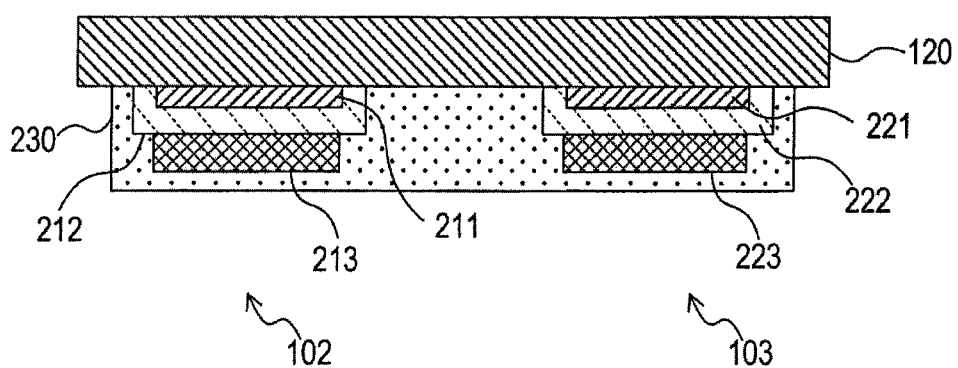
FIG. 3 is a cross-sectional view showing the structures of a first ammonia detection section 102 and a second ammonia detection section 103.

The sensor element unit 5 includes the NOx detection section 101, the first ammonia detection section 102, and the second ammonia detection section 103 (see FIG. 3).

The first ammonia detection section 102 and the second ammonia detection section 103 are disposed in parallel at substantially the same position as the reference electrode 143 in the longitudinal direction of the NOx detection section 101 (the horizontal direction in FIG. 2) in such a manner that the first ammonia detection section 102 and the second ammonia detection section 103 are located at different positions in the width direction of the NOx detection section 101 (the direction perpendicular to the sheet on which FIG. 2 is depicted). Therefore, in FIG. 2, of the first ammonia detection section 102 and the second ammonia detection section 103, only the first ammonia detection section 102 is shown.

The NOx detection section 101 is formed by sequentially stacking an insulating layer 113, a ceramic layer 114, an insulating layer 115, a ceramic layer 116, an insulating layer 117, a ceramic layer 118, an insulating layer 119, and an insulating layer 120. The insulating layers 113, 115, 117, 119, and 120 are formed mainly of alumina.

The NOx detection section 101 includes a first measurement chamber 121 formed between the ceramic layer 114 and the ceramic layer 116. In the NOx detection section 101, the exhaust gas is introduced from the outside into the interior of the first measurement chamber 121 through a diffusion resistor 122 that is disposed between the ceramic layer 114 and the ceramic layer 116 so as to be adjacent to the first measurement chamber 121. The diffusion resistor 122 is formed of a porous material such as alumina.

The NOx detection section 101 further includes a first pumping cell 130. The first pumping cell 130 includes a solid electrolyte layer 131 and pumping electrodes 132 and 133.

The solid electrolyte layer 131 is formed mainly of zirconia having oxygen ion conductivity. A part of the ceramic layer 114 is removed from a region exposed to the first measurement chamber 121, and the resulting space is filled with the solid electrolyte layer 131 instead of the ceramic layer 114.

The pumping electrodes 132 and 133 are formed mainly of platinum. The pumping electrode 132 is disposed on the solid electrolyte layer 131 so as to be exposed to the first measurement chamber 121. The pumping electrode 133 is disposed on the solid electrolyte layer 131 on the side opposite the pumping electrode 132 with the solid electrolyte layer 131 sandwiched between the pumping electrodes 132 and 133. The insulating layer 113 is removed from a region in which the pumping electrode 133 is disposed and from a region around the pumping electrode 133, and the resulting space is filled with a porous material 134 instead of the insulating layer 113. The porous material 134 allows gas (oxygen) migration between the pumping electrode 133 and the outside.

The NOx detection section 101 further includes an oxygen concentration detection cell 140. The oxygen concentration detection cell 140 includes a solid electrolyte layer 141, a detection electrode 142, and a reference electrode 143.

The solid electrolyte layer 141 is formed mainly of zirconia having oxygen ion conductivity. A part of the ceramic layer 116 is removed from a region on the rear end side (the right side of FIG. 2) of the solid electrolyte layer 131, and the resulting space is filled with the solid electrolyte layer 141 instead of the ceramic layer 116.

The detection electrode 142 and the reference electrode 143 are formed mainly of platinum. The detection electrode 142 is disposed on the solid electrolyte layer 141 so as to be exposed to the first measurement chamber 121. The reference electrode 143 is disposed on the solid electrolyte layer 141 on the side opposite the detection electrode 142 with the solid electrolyte layer 141 sandwiched between the detection electrode 142 and the reference electrode 143.

The NOx detection section 101 further includes a reference oxygen chamber 146. The reference oxygen chamber 146 is a through hole formed by removing the insulating layer 117 from a region in which the reference electrode 143 is disposed and from a region around the reference electrode 143.

The NOx detection section 101 further includes a second measurement chamber 148. The second measurement chamber 148 is formed rearward of the detection electrode 142 and the reference electrode 143 so as to pass through the solid electrolyte layer 141 and the insulating layer 117. In the NOx detection section 101, the exhaust gas discharged from the first measurement chamber 121 is introduced into the second measurement chamber 148.

The NOx detection section 101 further includes a second pumping cell 150. The second pumping cell 150 includes a solid electrolyte layer 151 and pumping electrodes 152 and 153.

The solid electrolyte layer 151 is formed mainly of zirconia having oxygen ion conductivity. The ceramic layer 118 is removed from a region exposed to the reference oxygen chamber 146 and the second measurement chamber 148 and a region around this exposed region, and the resulting space is filled with the solid electrolyte layer 151 instead of the ceramic layer 118.

The pumping electrodes 152 and 153 are formed mainly of platinum. The pumping electrode 152 is disposed on the solid electrolyte layer 151 so as to be exposed to the second measurement chamber 148. The pumping electrode 153 is disposed on the solid electrolyte layer 151 so as to be opposed to the reference electrode 143 with the reference oxygen chamber 146 therebetween. A porous material 147 is disposed inside the reference oxygen chamber 146 so as to cover the pumping electrode 153.

The NOx detection section 101 further includes a heater 160. The heater 160 is a heat-generating resistor that is formed mainly of platinum and generates heat when energized and is disposed between the insulating layers 119 and 120.

The first ammonia detection section 102 is formed on the outer surface of the NOx detection section 101, more specifically on the insulating layer 120. The first ammonia detection section 102 is disposed at substantially the same position, with respect to the direction of the axial line O (the horizontal direction in FIG. 2), as the reference electrode 143 in the NOx detection section 101.

The first ammonia detection section 102 includes a first reference electrode 211 formed on the insulating layer 120, a first solid electrolyte body 212 covering the front and side surfaces of the first reference electrode 211, and a first detection electrode 213 formed on the front surface of the first solid electrolyte body 212. The first ammonia detection section 102 detects the concentration of ammonia contained in the exhaust gas on the basis of a change in the electromotive force between the first reference electrode 211 and the first detection electrode 213.

Similarly, as shown in FIG. 3, the second ammonia detection section 103 includes a second reference electrode 221 formed on the insulating layer 120, a second solid electrolyte body 222 covering the front and side surfaces of the second reference electrode 221, and a second detection electrode 223 formed on the front surface of the second solid electrolyte body 222. The second ammonia detection section 103 detects the concentration of ammonia contained in the exhaust gas on the basis of a change in the electromotive force between the second reference electrode 221 and the second detection electrode 223.

The first reference electrode 211 and the second reference electrode 221 are formed mainly of platinum (Pt) serving as an electrode material and more specifically formed of a material containing Pt and zirconium oxide ($ZrO_2$). The first solid electrolyte body 212 and the second solid electrolyte body 222 are formed of an oxygen ion-conductive material such as yttria-stabilized zirconia (YSZ). The first detection electrode 213 and the second detection electrode 223 are formed mainly of gold (Au) serving as an electrode material and more specifically formed of a material containing Au and zirconium oxide ($ZrO_2$). The electrode materials of the first detection electrode 213 and the second detection electrode 223 are selected such that the first ammonia detection section 102 and the second ammonia detection section 103 differ from each other in terms of the ratio between the sensitivity to ammonia and the sensitivity to NOx.

The first ammonia detection section 102 and the second ammonia detection section 103 are covered with a porous protecting layer 230. The protecting layer 230 is configured to prevent adhesion of a poisoning material to the first detection electrode 213 and the second detection electrode 223 and to control the diffusion rate of ammonia flowing from the outside into the first ammonia detection section 102 and the second ammonia detection section 103.

As shown in FIG. 2, the control section 3 includes a control circuit 180 and a microcomputer 190.

The control circuit 180 is an analog circuit disposed on a circuit board. The control circuit 180 includes an Ip1 drive circuit 181, a Vs detection circuit 182, a reference voltage comparator 183, an Icp supply circuit 184, a Vp2 application circuit 185, an Ip2 detection circuit 186, a heater drive circuit 187, and an electromotive force detection circuit 188.

The pumping electrode 132, the detection electrode 142, and the pumping electrode 152 are connected to a reference potential. The pumping electrode 133 is connected to the Ip1 drive circuit 181. The reference electrode 143 is connected to the Vs detection circuit 182 and the Icp supply circuit 184. The pumping electrode 153 is connected to the Vp2 application circuit 185 and the Ip2 detection circuit 186. The heater 160 is connected to the heater drive circuit 187.

The Ip1 drive circuit 181 applies a voltage Vp1 between the pumping electrode 132 and the pumping electrode 133 to supply a first pumping current Ip1 and detects the supplied first pumping current Ip1.

The Vs detection circuit 182 detects the voltage Vs between the detection electrode 142 and the reference electrode 143 and outputs the detection result to the reference voltage comparator 183.

The reference voltage comparator 183 compares a reference voltage (e.g., 425 mV) with the output from the Vs detection circuit 182 (the voltage Vs) and outputs the comparison result to the Ip1 drive circuit 181. The Ip1 drive circuit 181 controls the direction and magnitude of the first pumping current Ip1 such that the voltage Vs becomes equal to the reference voltage to thereby adjust the concentration of oxygen in the first measurement chamber 121 to a prescribed value at which decomposition of NOx does not occur.

The Icp supply circuit 184 causes a weak current Icp to flow between the detection electrode 142 and the reference electrode 143. Oxygen is thereby fed from the first measurement chamber 121 to the reference oxygen chamber 146 through the solid electrolyte layer 141, and the concentration of oxygen in the reference oxygen chamber 146 is set to be a prescribed oxygen concentration serving as a reference.

The Vp2 application circuit 185 applies a constant voltage Vp2 (e.g., 450 mV) between the pumping electrode 152 and the pumping electrode 153. In the second measurement chamber 148, NOx is dissociated (reduced) through the catalytic action of the pumping electrodes 152 and 153 included in the second pumping cell 150. The oxygen ions obtained as a result of the dissociation migrate in the solid electrolyte layer 151 between the pumping electrode 152 and the pumping electrode 153, so that a second pumping current Ip2 flows. The Ip2 detection circuit 186 detects the second pumping current Ip2.

The heater drive circuit 187 applies a positive voltage for heater energization to one end of the heater 160, which is a heat-generating resistor, and applies a negative voltage for heater energization to the other end of the heater 160 to thereby drive the heater 160.

The electromotive force detection circuit 188 detects the electromotive force between the first reference electrode 211 and the first detection electrode 213 (hereinafter referred to as a first ammonia electromotive force) and the electromotive force between the second reference electrode 221 and the second detection electrode 223 (hereinafter referred to as a second ammonia electromotive force), and outputs signals representing the detection results to the microcomputer 190.

The microcomputer 190 includes a CPU 191, a ROM 192, a RAM 193, and a signal input/output unit 194.

The CPU 191 executes a process for controlling the sensor element unit 5 according to a program stored in the ROM 192. The signal input/output unit 194 is connected to the Ip1 drive circuit 181, the Vs detection circuit 182, the Ip2 detection circuit 186, the heater drive circuit 187, and the electromotive force detection circuit 188. The CPU 191 outputs a driving signal to the heater drive circuit 187 through the signal input/output unit 194 so as to control the electric power supplied to the heater 160 by means of pulse width modulation such that the heater 160 reaches a target temperature.

The CPU 191 reads various data from the ROM 192 and performs various computation processes on the basis of the value of the first pumping current Ip1, the value of the second pumping current Ip2, the first ammonia electromotive force, and the second ammonia electromotive force.

The ROM 192 stores a "first ammonia electromotive force–first ammonia concentration output relational expression," a "second ammonia electromotive force–second ammonia concentration output relational expression," a "first pumping current (Ip1)–oxygen concentration output relational expression," a "second pumping current (Ip2)–NOx concentration output relational expression," a "first ammonia concentration output & second ammonia concentration output & oxygen concentration output–corrected ammonia concentration output relational expression" (correction expression (1): see the description below), a "first ammonia concentration output & second ammonia concentration output & oxygen concentration output–corrected $NO_2$ concentration output relational expression" (correction expression (2)), an "NOx concentration output & corrected ammonia concentration output & corrected $NO_2$ concentration output-corrected NOx concentration output relational expression" (correction expression (3)).

Notably, the various data may be set in the form of predetermined relational expressions as described above or may be set in other forms (for example, tables) so long as various gas concentrations can be calculated from the outputs of the sensor. Alternatively, they may be values (relational expressions, tables, etc.) obtained through use of a model gas whose gas concentration is known.

The "first ammonia electromotive force–first ammonia concentration output relational expression" and the "second ammonia electromotive force–second ammonia concentration output relational expression" are expressions representing the relation between the ammonia electromotive forces output from the first ammonia detection section 102 and the second ammonia detection section 103 and an ammonia concentration output representing the ammonia concentration in the exhaust gas.

The "first pumping current–oxygen concentration output relational expression" is an expression representing the relation between the first pumping current and the oxygen concentration in the exhaust gas. The "second pumping current–NOx concentration output relational expression" is an expression representing the relation between the second pumping current and the NOx concentration in the exhaust gas.

The "first ammonia concentration output & second ammonia concentration output & oxygen concentration output-corrected ammonia concentration output relational expression" is an expression representing the relation between the (first, second) ammonia concentration output affected by the oxygen concentration and the $NO_2$ concentration and the corrected ammonia concentration output from which the influences of the oxygen concentration and the $NO_2$ concentration have been removed.

The "first ammonia concentration output & second ammonia concentration output & oxygen concentration output-corrected $NO_2$ concentration output relational expression" is an expression representing the relation between the $NO_2$ concentration output affected by the oxygen concentration and the ammonia concentration and the corrected $NO_2$ concentration output from which the influences of the oxygen concentration and the ammonia concentration have been removed. The "NOx concentration output & corrected ammonia concentration output & corrected $NO_2$ concentration output-corrected NOx concentration output relational expression" is an expression representing the relation between the NOx concentration output affected by the ammonia concentration and the $NO_2$ concentration and the accurate corrected NOx concentration output from which the influences of the ammonia concentration and the $NO_2$ concentration have been removed for correction.

Next, there will be described a computation process which is executed by the CPU 191 of the microcomputer 190 so as to obtain the NOx concentration and the ammonia concentration from the first pumping current Ip1, the second pumping current Ip2, the first ammonia electromotive force, and the second ammonia electromotive force.

When the first pumping current Ip1, the second pumping current Ip2, the first ammonia electromotive force, and the second ammonia electromotive force are input, the CPU 191 performs a computation process for obtaining the oxygen concentration output, the NOx concentration output, the first ammonia concentration output, and the second ammonia concentration output. Specifically, the CPU 191 calls the "first ammonia electromotive force–first ammonia concentration output relational expression," the "second ammonia electromotive force–second ammonia concentration output relational expression," the "first pumping current Ip1 –oxygen concentration output relational expression," and the "second pumping current Ip2–NOx concentration output relational expression" from the ROM 192, and calculates the respective concentration outputs through use of these relational expressions. Subsequently, when the oxygen concentration output, the NOx concentration output, the first ammonia concentration output, and the second ammonia concentration output are obtained, the CPU 191 obtains the ammonia concentration and the NOx concentration in the exhaust gas by performing computation using correction expressions described below.

$$x = F(A, B, D) \qquad \text{Correction expression (1)}$$
$$= (eA - c) * (jB - h - fA + d)/$$
$$(eA - c - iB + g) + fA - d$$

$$y = F'(A, B, D) \qquad \text{Correction expression (2)}$$
$$= (jB - h - fA + d)/(eA - c - iB + g)$$

$$z = C - ax + by \qquad \text{Correction expression (3)}$$

In these correction expressions, x represents the ammonia concentration, y represents the $NO_2$ concentration, and z represents the NOx concentration. A represents the first ammonia concentration output, B represents the second ammonia concentration output, C represents the NOx concentration output, and D represents the oxygen concentration output. F in the correction expression (1) represents that x is a function of A, B, and D, and F' in the correction expression (2) represents that y is a function of A, B, and D. a and b are correction coefficients, and c, d, e, f, g, h, i, and j are coefficients calculated through use of the oxygen concentration output D (namely, coefficients determined by D).

The CPU 191 obtains the ammonia concentration and the NOx concentration in the exhaust gas by substituting the first ammonia concentration output (A), the second ammonia concentration output (B), the NOx concentration output (C), and the oxygen concentration output (D) into the above-described correction expressions (1) to (3).

Notably, the correction expression (1) and the correction expression (2) are expressions determined on the basis of the characteristics of the first ammonia detection section 102 and the second ammonia detection section 103, and the correction expression (3) is an expression determined on the basis of the characteristics of the NOx detection section 101. The correction expressions (1) to (3) are mere examples of correction expressions, and other correction expressions, coefficients, etc. may be properly changed in accordance with the gas detection characteristics.

Since a publicly known method for computing the NOx concentration and the $NO_2$ concentration is described in, for example, Japanese Patent Application Laid-Open (kokai) No. 2015-034814, its detailed description is omitted.

The microcomputer 190 executes an ammonia concentration calculation process for calculating the ammonia concentration in the exhaust gas. The steps of the ammonia concentration calculation process will now be described. The ammonia concentration calculation process is started immediately after the microcomputer 190 starts its operation.

Figure 4:
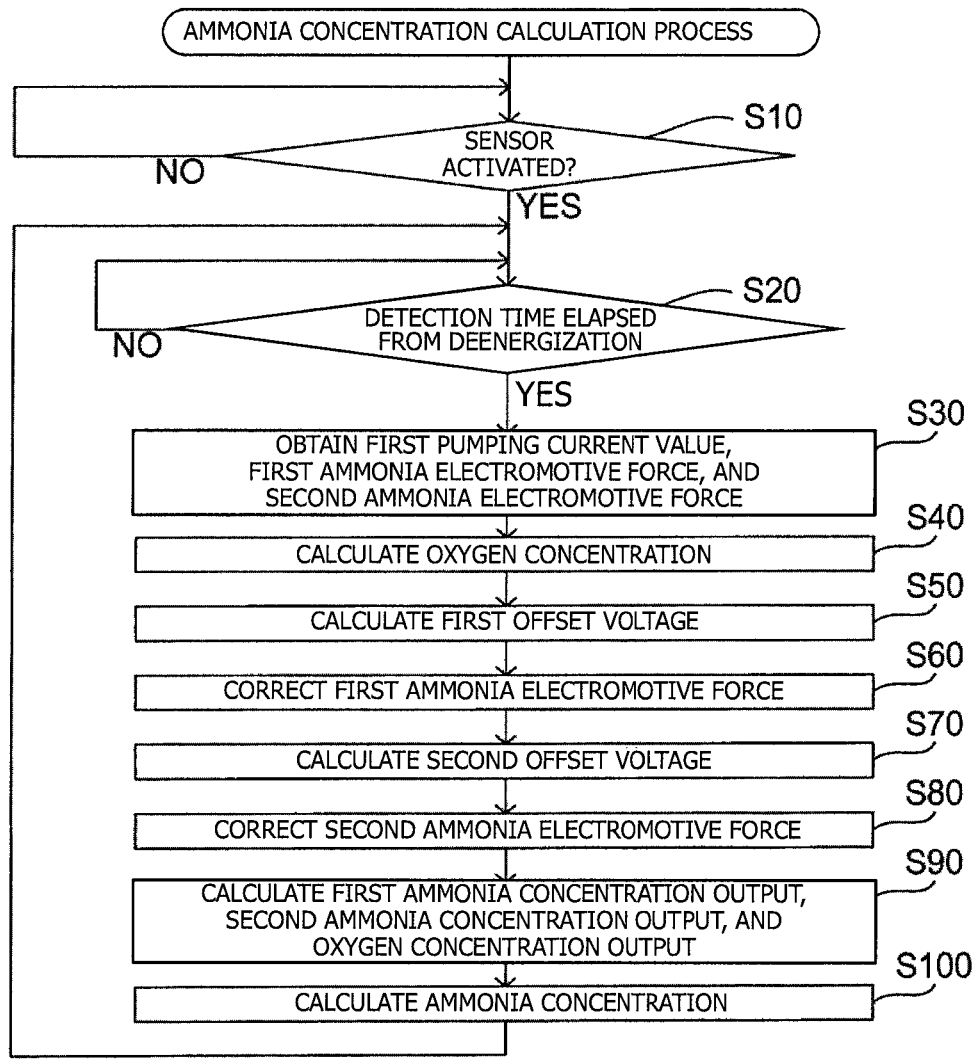
FIG. 4 is a flowchart showing the processing of calculating the concentration of ammonia.

When this ammonia concentration calculation process is executed, as shown in FIG. 4, the CPU 191 of the microcomputer 190 first determines in S10 whether or not the sensor element unit 5 has become active. In the case where the sensor element unit 5 has not yet become active, the CPU 191 waits until the sensor element unit 5 becomes active by repeating the process of S10. When the sensor element unit 5 becomes active, in S20, the CPU 191 determines whether or not a detection time set in advance has elapsed after the heater 160 had been switched from the energized state (ON state) to the deenergized state (OFF state). The detection time is set to be shorter than a half of the modulation period of the pulse width modulation. Namely, the detection time is shorter than a time between a point in time when the heater 160 is switched from the ON state to the OFF state and a point in time when the heater 160 is then switched from the OFF state to the ON state. In the case where the detection time has not yet elapsed, the CPU 191 waits until the detection time elapses by repeating the process of S20.

When the detection time has elapsed, in S30, the CPU 191 obtains the detection signal representing the value of the first pumping current Ip1 (hereinafter referred to as the "first pumping current value") from the Ip1 drive circuit 181, and obtains the detection signals representing the first ammonia electromotive force and the second ammonia electromotive force from the electromotive force detection circuit 188. Further, in S40, the CPU 191 calculates the oxygen concentration on the basis of the detection signal representing the "first pumping current value" and the "first pumping current Ip1–oxygen concentration output relational expression."

Next, in S50, the CPU 191 obtains the detection signal representing the value of the output voltage of the power supply from the heater drive circuit 187, and calculates an offset voltage of the first ammonia detection section 102 (hereinafter referred to as the "first offset voltage") on the basis of the output voltage of the power supply (the peak value of the voltage waveform of the pulse-width-modulated voltage applied to the heater 160) and the oxygen concentration calculated in S60.

Figure 5:
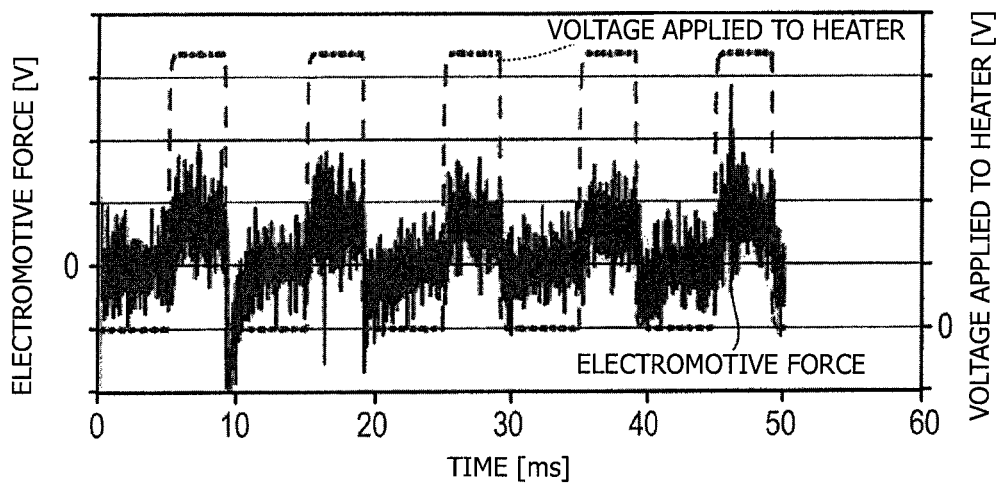
FIG. 5 is a graph showing changes in voltage applied to a heater 160 and ammonia electromotive force with time.

Incidentally, as shown in FIG. 5, the values of the first ammonia electromotive force and the second ammonia electromotive force change greatly at the timing when the heater 160 is switched from the ON state to the OFF state and the timing when the heater 160 is switched from the OFF state to the ON state.

Figure 6:
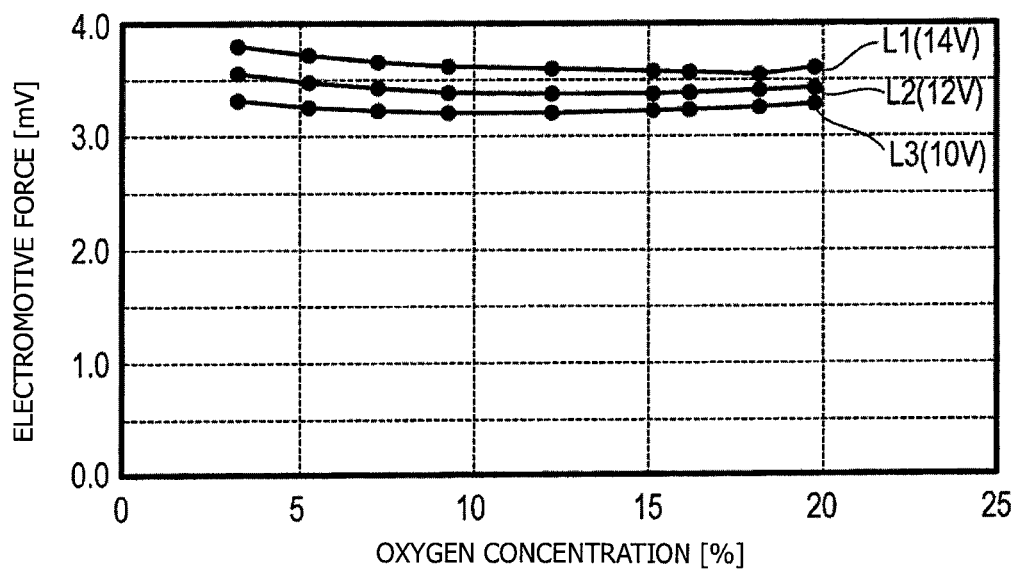
FIG. 6 is a graph showing the relation between ammonia electromotive force and oxygen concentration for different output voltages of a power supply.

FIG. 6 is a graph showing the relation between the first and second ammonia electromotive forces and the oxygen concentration which were measured for different output voltages of the power supply when the above-mentioned detection time had elapsed after the switching of the heater 160 from the ON state to the OFF state. Curves L1, L2, and L3 of FIG. 6 respectively show the relation between the ammonia electromotive force and the oxygen concentration when the output voltage of the power supply was 14 V, 12 V, and 10 V.

On the basis of the results of the measurement shown in FIG. 6, a relational expression representing the relation among the offset voltage Vo, the power supply output voltage Vn, and the oxygen concentration Co is set as shown in the following expression (4). The coefficients a, b, c, d, and e of the following expression (4) are coefficients for representing the results of the measurement shown in FIG. 6 by a relational expression.

$$Vo = (a \times Co_2 + b \times Co + c) + (14 - Vn) \times (d \times Co + e) \quad (4)$$

In S50, the CPU 191 calculates the first offset voltage by substituting the power supply output voltage and the oxygen concentration into the relational expression (4).

After completion of the process of S50, as shown in FIG. 4, in S60, the CPU 191 calculates the first corrected ammonia electromotive force by subtracting the first offset voltage calculated in S50 from the first ammonia electromotive force.

In S70, the CPU 191 calculates an offset voltage of the second ammonia detection section 103 (hereinafter referred to as the "second offset voltage") in the same manner as in S50. Further, in S80, the CPU 191 calculates the second corrected ammonia electromotive force by subtracting the second offset voltage calculated in S70 from the second ammonia electromotive force in the same manner as in S60.

In S90, the CPU 191 calculates the first ammonia concentration output on the basis of the first corrected ammonia electromotive force and the "first ammonia electromotive force–first ammonia concentration output relational expression." Also, in S90, the CPU 191 calculates the second ammonia concentration output on the basis of the second corrected ammonia electromotive force and the "second ammonia electromotive force–second ammonia concentration output relational expression." Further, in S90, the CPU 191 calculates the oxygen concentration output on the basis of the first pumping current value and the "first pumping current Ip1–oxygen concentration output relational expression."

Further, in S100, the CPU 191 calculates the ammonia concentration in the exhaust gas on the basis of the correction expression (1) and the first ammonia concentration output, the second ammonia concentration output, and the oxygen concentration output calculated in S90, and then proceeds to S20.

The multi-gas detection apparatus 1 configured as described above includes the first solid electrolyte body 212; the first reference electrode 211 and the first detection electrode 213 disposed on the first solid electrolyte body 212 and forming a pair; the second solid electrolyte body 222; the second reference electrode 221 and the second detection electrode 223 disposed on the second solid electrolyte body 222 and forming a pair; and the heater 160 for heating the first solid electrolyte body 212 and the second solid electrolyte body 222. In the multi-gas detection apparatus 1, the temperature of the first solid electrolyte body 212 is controlled as a result of pulse width modulation control of the electric power supplied from the power supply to the heater 160, and the concentration of ammonia is detected through use of the electromotive force of the first ammonia detection section 102; i.e., the electromotive force generated between the first reference electrode 211 and the first detection electrode 213 in accordance with the ammonia concentration in the exhaust gas. Also, in the multi-gas detection apparatus 1, the temperature of the second solid electrolyte body 222 is controlled as a result of pulse width modulation control of the electric power supplied from the power supply to the heater 160, and the concentration of ammonia is detected through use of the electromotive force of the second ammonia detection section 103; i.e., the electromotive force generated between the second reference electrode 221 and the second detection electrode 223 in accordance with the ammonia concentration in the exhaust gas.

The multi-gas detection apparatus 1 calculates the amount of a change (namely, the first offset voltage and the second offset voltage) in the ammonia electromotive force (namely, the first ammonia electromotive force and the second ammonia electromotive force) caused by a change in the power supply output voltage (S50, S70). Also, the multi-gas detection apparatus 1 corrects the ammonia electromotive forces generated at the first ammonia detection section 102 and the second ammonia detection section 103 through use of the calculated change amount (S60, S80).

As a result, the multi-gas detection apparatus 1 can reduce the influence of changes in the ammonia electromotive force which occur due to the supply of electric power to the heater 160 by pulse width modulation, to thereby improve the accuracy in detecting the ammonia concentration.

Also, the multi-gas detection apparatus 1 detects the oxygen concentration in the exhaust gas (S40). The multi-gas detection apparatus 1 corrects the offset voltage on the basis of the detected oxygen concentration (S50, S70).

As a result, the multi-gas detection apparatus 1 can reduce the influence of changes in the ammonia electromotive force which occur when the impedances of the first ammonia detection section 102 and the second ammonia detection section 103 change in accordance with the oxygen concentration in the exhaust gas, to thereby further improve the accuracy in detecting the ammonia concentration.

Also, the multi-gas detection apparatus 1 corrects the first ammonia electromotive force by subtracting the first offset voltage from the first ammonia electromotive force, and corrects the second ammonia electromotive force by subtracting the second offset voltage from the second ammonia electromotive force. As a result, the multi-gas detection apparatus 1 can correct the ammonia electromotive force by a simple computation of subtracting the offset voltage from the ammonia electromotive force, to thereby reduce the computation processing load of the multi-gas detection apparatus 1.

Also, the multi-gas detection apparatus 1 corrects the ammonia electromotive force through use of the ammonia electromotive force after the detection time set in advance elapses from the point in time when the heater 160 has been switched from the ON state to the OFF state by the pulse width modulation.

As described above, the multi-gas detection apparatus 1 detects the ammonia concentration through use of the ammonia electromotive force detected when no electric power is supplied to the heater 160. Therefore, the multi-gas detection apparatus 1 can reduce the influence of changes in the ammonia electromotive force which occur due to the flow of current to the heater 160, to thereby further improve the accuracy in detecting the ammonia concentration.

In the above-described embodiment, the multi-gas detection apparatus 1 corresponds to the gas detection apparatus in the present invention; the first ammonia detection section 102 and the second ammonia detection section 103 correspond to the gas sensor in the present invention; the first solid electrolyte body 212 and the second solid electrolyte body 222 correspond to the solid electrolyte body in the present invention; and the first reference electrode 211 and the first detection electrode 213 and the second reference electrode 221 and the second detection electrode 223 correspond to the pair of electrodes in the present invention.

The processes of S50 and S70 carried out by CPU 191 correspond to the step of calculating the amount of a change in the electromotive force caused by a change in an output voltage of the power supply that is performed by the change amount calculation section in the present invention; the processes of S60 and S80 carried out by CPU 191 correspond to the step of correcting the electromotive force generated in the gas sensor that is performed by the correction section in the present invention; and the process of S40 carried out by CPU 191 corresponds to the step of detecting the concentration of oxygen in the atmosphere of interest that is performed by the oxygen detection section in the present invention.

The exhaust gas corresponds to the atmosphere of interest in the present invention; ammonia corresponds to the detection target gas in the present invention; the first ammonia electromotive force and the second ammonia electromotive force correspond to the electromotive force in the present invention; and the first offset voltage and the second offset voltage correspond to the change amount in the present invention.

While the embodiment of the present invention has been described, the present invention is not limited to the embodiment. The present invention can be implemented in various forms so long as they fall within the technical scope of the invention.

For example, in the above-described embodiment, the first ammonia detection section 102 having a structure in which the first reference electrode 211, the first solid electrolyte body 212, and the first detection electrode 213 are stacked and the second ammonia detection section 103 having a structure in which the second reference electrode 221, the second solid electrolyte body 222, and the second detection electrode 223 are stacked are used to detect the concentration of ammonia. However, the present invention is not limited to gas sensors for detecting the concentration of ammonia. Namely, the present invention can be applied to any gas sensor in which an electromotive force is generated between a pair of electrodes in accordance with the concentration of a detection target gas in an atmosphere of interest.

In the above-described embodiment, the first ammonia detection section 102 and the second ammonia detection section 103 are formed on the outer surface of the NOx detection section 101. However, the present invention is not limited to the ammonia detection sections formed on the gas sensor. The first ammonia detection section 102 and the second ammonia detection section 103 may be formed on any electrically insulating member.

In the above-described embodiment, the first offset voltage and the second offset voltage are calculated by substituting the power supply output voltage and the oxygen concentration into the relational expression (4). However, the method of calculating the first offset voltage and the second offset voltage is not limited thereto. For example, the first offset voltage and the second offset voltage may be calculated by referring to a map in which the relation among the power supply output voltage, the oxygen concentration, and the first and second offset voltages is set in advance.

DESCRIPTION OF REFERENCE NUMERALS

1: multi-gas detection apparatus
2: multi-gas sensor
3: control section
102: first ammonia detection section
103: second ammonia detection section
190: microcomputer
211: first reference electrode
212: first solid electrolyte body
213: first detection electrode
221: second reference electrode
222: second solid electrolyte body
223: second detection electrode

The invention claimed is:

1. A gas detection apparatus for detecting a concentration of a target gas in an atmosphere of interest comprising:
a gas sensor having a solid electrolyte body;
a pair of electrodes disposed on the solid electrolyte body;
a heater for heating the solid electrolyte body;
a change amount calculation section;
a correction section; and
an oxygen detection section which detects a concentration of oxygen in the atmosphere of interest, wherein
electric power supplied from a power supply to the heater is controlled by pulse width modulation so as to control a temperature of the solid electrolyte body,
the concentration of the target gas is detected through use of an electromotive force generated between the pair of electrodes in accordance with the concentration of the target gas,
the change amount calculation section calculates the amount of a change in the electromotive force caused by a change in an output voltage of the power supply on the basis of the concentration of oxygen detected by the oxygen detection section, and
the correction section corrects the electromotive force generated in the gas sensor through use of the change amount calculated by the change amount calculation section.

2. The gas detection apparatus according to claim 1, wherein the correction section corrects the electromotive force by subtracting the change amount calculated by the change amount calculation section from the electromotive force generated in the gas sensor.

3. The gas detection apparatus according to claim 2, wherein the correction section corrects the electromotive force through use of the electromotive force detected after elapse of a detection time set in advance from a point in time at which the heater is switched from an energized state to a deenergized state by the pulse width modulation.

4. The gas detection apparatus according to claim 1, wherein the correction section corrects the electromotive force through use of the electromotive force detected after elapse of a detection time set in advance from a point in time at which the heater is switched from an energized state to a deenergized state by the pulse width modulation.

* * * * *